United States Patent [19]

Deruelle et al.

[11] Patent Number: 5,274,123
[45] Date of Patent: Dec. 28, 1993

[54] PROCESS FOR THE PREPARATION OF CYCLIC SULPHATES

[75] Inventors: Roger Deruelle, La Queue en Brie; Michel Guinard, Thiais; Gerard Perrier, Evry, all of France

[73] Assignee: Rhone-Poulenc Rorer, S.A., France

[21] Appl. No.: 956,027

[22] PCT Filed: Jul. 8, 1991

[86] PCT No.: PCT/FR91/00549
§ 371 Date: Dec. 10, 1992
§ 102(e) Date: Dec. 10, 1992

[87] PCT Pub. No.: WO92/00975
PCT Pub. Date: Jan. 23, 1992

[30] Foreign Application Priority Data

Jul. 9, 1990 [FR] France .................. 90 08686

[51] Int. Cl.$^5$ .......................... C07D 327/10
[52] U.S. Cl. .................................. 549/34
[58] Field of Search ............................ 549/34

[56] References Cited

U.S. PATENT DOCUMENTS

| | | | |
|---|---|---|---|
| 3,045,027 | 7/1962 | Ham | 549/34 |
| 3,100,780 | 8/1963 | Klass | 549/11 |
| 3,154,526 | 10/1964 | Klass | 528/377 |
| 3,167,572 | 1/1965 | Klass | 549/34 |
| 4,924,007 | 5/1990 | Massonneau et al. | 549/34 |

FOREIGN PATENT DOCUMENTS 343053 11/1989 European Pat. Off. ............. 549/34
2040503 2/1972 Fed. Rep. of Germany.

OTHER PUBLICATIONS

"The Merck Index," 10th ed., M. Windholz et al. eds., p. 1289 entry no. 8860, Merck & Co., Rahway, N.J. (1983).

Primary Examiner—Richard L. Raymond
Attorney, Agent, or Firm—Morgan & Finnegan

[57] ABSTRACT

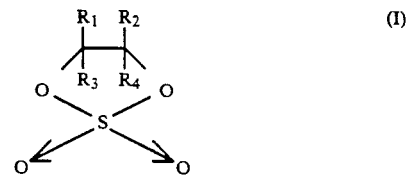

A method for preparing cyclic sulphates having general formula (I), wherein sulphuric anhydride and an alkylene oxide are simultaneously added to the dioxane. In general formula (I), $R_1$, $R_2$, $R_3$ and $R_4$ are the same or different and are a hydrogen atom of a $C_{1-4}$ alkyl radical optionally substituted by a halogen atom.

4 Claims, No Drawings

PROCESS FOR THE PREPARATION OF CYCLIC SULPHATES

FIELD OF THE INVENTION

The present invention relates to a process for the preparation of cyclic sulphates of general formula:

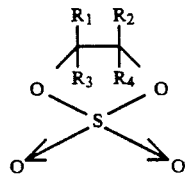

in which $R_1$, $R_2$, $R_3$ and $R_4$, which are identical or different, denote a hydrogen atom or an alkyl radical containing 1 to 4 carbon atoms, optionally substituted by a halogen atom.

BACKGROUND OF THE INVENTION

It is known to prepare cyclic sulphates by reaction of sulphuric anhydride with an alkylene oxide, the operation being carried out in dioxane (U.S. Pat. No. 3,045,027) or in another organic solvent such as in dichloroethane (U.S. Pat. No. 3,154,526 or U.S. Pat. No. 3,167,572) or in gaseous phase at a temperature below 140° C. (U.S. Pat. No. 3,100,780). However, these processes do not make it possible to obtain cyclic sulphates in satisfactory yields.

DETAILED DESCRIPTION OF THE INVENTION

It is now been found, and this is what forms the subject of the present invention, that cyclic sulphates of general formula (I) can be obtained in yields which are generally higher than 80% by simultaneously adding sulphuric anhydride and the alkylene oxide to dioxane, optionally in the presence of a halogenated aliphatic hydrocarbon such as 1,2-dichloroethane.

To make use of the process according to the invention it is particularly important to operate under well-defined conditions.

More precisely, the molar ratio of sulphuric anhydride to the alkylene oxide must be maintained at a constant value of between 1.01 and 1.07 throughout the addition period. It is advantageous to maintain the ratio in the vicinity of 1.04.

A quantity of dioxane is generally employed such that the molar ratio of dioxane to the alkylene oxide used is between 1 and 30. When ethylene oxide is employed as the alkylene oxide the ratio is preferably close to 7.

The reaction temperature is generally between 30 and 60° C., preferably between 40 and 50° C.

It is particularly advantageous to employ anhydrous dioxane, which can be obtained, for example, by azeotropic distillation before the introduction of sulphuric anhydride and of the alkylene oxide.

The sulphuric anhydride employed is preferably technical anhydride which is in liquid form (practically free from linear and/or crosslinked polymers).

The alkylene oxide employed may be introduced in liquid or gaseous form, depending on its nature.

The cyclic sulphate of general formula (I) obtained by making use of the process according to the invention may be either employed as it is after removal of dioxane by fast distillation, or purified by dissolving, after flash distillation of the dioxane, in a suitable organic solvent such as a halogenated aliphatic hydrocarbon like methylene chloride, followed by washing of the organic solution with sulphuric acid, optionally in aqueous solution, and then with water until neutral: the cyclic sulphate is obtained after evaporation of the solvent.

The process according to the invention is particularly useful for preparing ethylene sulphate, propylene sulphate and 1-chloromethylethylene sulphate.

EXAMPLES

The following examples, given without any limitation being implied, show how the invention can be put into practice.

Example 1

2000 g (22.7 moles of dioxane) are introduced into a 2.5-liter glass reactor fitted with a stirrer. 500 g of dioxane are distilled off at atmospheric pressure in order to remove the water present in the solvent. After cooling the residual dioxane (1500 g; 17.0 moles) to 45° C., 189 g of sulphuric anhydride (2.36 moles) and 100 g of ethylene oxide (2.27 moles) are added in parallel in 100 minutes while the sulphuric anhydride/ethylene oxide molar ratio is kept strictly equal to 1.04 and while the temperature is maintained at 45° C.

When the addition is complete, the reaction mixture is stirred for another 30 minutes at 45° C.

After cooling, the determination of the reaction mixture
- by high performance chromatography (HPLC) shows that the yield of ethylene sulphate is 90% relative to the ethylene oxide used,
- by gas phase chromatography (GPC) shows that the degree of conversion of ethylene oxide is 100%.

After removal of dioxane by distillation at reduced pressure (20 mm Hg; 2.6 kPa), the crude ethylene sulphate, which is 82% pure, is extracted with 1200 g of dichloromethane. The chloromethylene solution is washed with concentrated sulphuric acid and then with water and is finally dried over sodium sulphate. After filtering and concentrating to dryness, 232 g of ethylene sulphate are obtained in the form of a white powder melting at 99° C., its purity being 97%.

Example 2

2100 g of dioxane (23.9 moles) are introduced into a 2.5-liter glass reactor fitted with a stirrer. 300 g of dioxane are distilled off at atmospheric pressure in order to remove the water present in the solvent. After cooling the residual dioxane (1800 g; 20.5 moles) to 40° C., 77.8 g of sulphuric anhydride (0.97 moles) and 40 g of ethylene oxide (0.91 moles) are added in parallel in 60 minutes, while the sulphuric anhydride/ethylene oxide molar ratio is kept strictly equal to 1.07 throughout the addition period and while the temperature is maintained at 40° C.

When the addition is complete, the reaction mixture is stirred for another 30 minutes at 40° C.

After cooling, the determination of the reaction mixture:
- by HPLC shows that the yield of ethylene sulphate is 95% relative to the ethylene oxide used,
- by GPC the degree of conversion of ethylene oxide is 100%.

After removal of the dioxane by distillation at reduced pressure (20 mm Hg; 2.6 kPa), the crude ethylene sulphate, which is 88% pure, is extracted with 500 g of dichloromethane. The chloromethylene solution is washed with concentrated sulphuric acid and then with water until neutral and is finally dried over sodium sulphate. After filtering and removing the solvents, 103.5 g of ethylene sulphate are obtained in the form of a white powder melting at 99° C., its purity being 97%.

Example 3

1800 g of dioxane (20.5 moles) are introduced into a 2.5-liter glass reactor fitted with a stirrer. 300 g of dioxane are distilled off at atmospheric pressure in order to remove the water present in the solvent. After cooling the residual dioxane (1500 g; 17.0 moles) to 45° C., 189 g of sulphuric anhydride (2.36 moles) and 132 g of propylene oxide (2.26 moles) are added in parallel in 100 minutes, while a sulphuric anhydride/propylene oxide molar ratio is kept strictly equal to 1.04 throughout the addition period and while the temperature is maintained at 45° C.

When the addition is complete, the reaction mixture is stirred for another 30 minutes at 45° C.

After cooling, the determination of the reaction mixture by HPLC shows that the yield of propylene sulphate is 76% relative to the propylene oxide used, After the usual treatment, propylene sulphate is obtained, its boiling point being 80° C. at a pressure of 1 mm Hg (0.3 kPa).

Example 4

1800 g (20.5 moles) of dioxane are introduced into a 2.5-liter glass reactor fitted with a stirrer. 300 g of dioxane are distilled off at atmospheric pressure in order to remove the water present in the solvent. After cooling the residual dioxane (1500 g; 17.0 moles) to 45° C., 189 g of sulphuric anhydride (2.36 moles) and 210 g of epichlorohydrin (2.27 moles) are added in parallel in 100 minutes, the sulphuric anhydride/epichlorohydrin molar ratio being kept strictly equal to 1.04 throughout the addition period and the temperature being maintained at 45° C.

When the addition is complete, the reaction mixture is stirred for another 30 minutes at 45° C.

After cooling, determination of the reaction mixture by HPLC shows that the yield of 1-chloromethylethylene sulphate is 79% relative to the epichlorohydrin used.

After the usual treatment, 1-chloromethylethylene sulphate which has the following characteristics is obtained:

- infrared spectrum (in solution in dichloromethane): characteristic absorption bands at 1398, 1214, 891, 651 and 535 $cm^{-1}$,

- mass spectrum (i.e.):M/Z (%)=172(8), 123(100), 137(5).

Example 5

208 g (2.36 moles) of dioxane and 1263 g of 1,2-dichloroethane (1000 $cm^3$) are introduced into a 2.5-liter glass reactor fitted with a stirrer. The reaction mixture is heated to 45° C. 189 g of sulphuric anhydride (2.36 moles) and 132 g of propylene oxide (2.26 moles) are introduced in parallel in 70 minutes, the sulphuric anhydride/propylene oxide molar ratio being kept strictly equal to 1.04 throughout the addition period and the temperature being maintained at 45° C.

When the addition is complete, the reaction mixture is stirred for another 30 minutes at 45° C.

After cooling, determination of the reaction mixture by HPLC shows that the yield of propylene sulphate is 84% relative to the propylene oxide used.

Example 6

208 g (2.36 moles) of dioxane and 1263 g of 1,2-dichloroethane (1000 $cm^3$) are introduced into a 2.5-liter glass reactor fitted with a stirrer. The reaction mixture is heated to 45° C. 189 g of sulphuric anhydride (2.36 moles) and 210 g of epichlorohydrin (2.27 moles) are introduced in parallel in 69 minutes, the sulphuric anhydride/epichlorohydrin molar ratio being kept strictly equal to 1.04 throughout the addition period and the temperature being maintained at 45° C.

When the addition is complete, the reaction mixture is stirred for another 30 minutes at 45° C.

After cooling, determination of the reaction mixture by HPLC shows that the yield of 1-chloromethylethylene sulphate is 87% relative to the epichlorohydrin used.

Although the invention has been described in conjunction with specific embodiment, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the preparation of a cyclic sulphate of formula

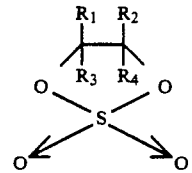

in which $R_1$, $R_2$, $R_3$ and $R_4$, which are identical or different, denote a hydrogen atom or an alkyl radical containing 1 to 4 carbon atoms, optionally substituted by a halogen atom, comprising reacting sulphuric anhydride with an alkylene oxide, and adding sulphuric anhydride and the alkylene oxide simultaneously to dioxane, optionally in the presence of a halogenated aliphatic hydrocarbon, the molar ratio of sulphuric anhydride to the alkylene oxide is constant and is between 1.01 and 1.07 throughout the addition period.

2. Process according to claim 1, wherein the molar ratio of dioxane to the alkylene oxide is between 1 and 30.

3. Process according to claim 1, wherein the operation is carried out at a temperature of between 30 and 60° C.

4. Process according to claim 1, for the preparation of ethylene sulphate, propylene sulphate and 1-chloromethylethylene sulphate.

* * * * *